United States Patent [19]

Varasi et al.

[11] Patent Number: 5,446,066
[45] Date of Patent: * Aug. 29, 1995

[54] SUBSTITUTED (ARYLALKOXYBENZYL)AMINOPROPANAMIDE DERIVATIVES AND PROCESS FOR THEIR PREPARATION

[75] Inventors: Mario Varasi, Milan, Italy; Philippe Dostert, Paris, France; Paolo Pevarello, Pavia; Alberto Bonsignori, Milan, both of Italy

[73] Assignee: Farmitalia Carlo Erba S.r.l., Milan, Italy

[*] Notice: The portion of the term of this patent subsequent to Aug. 17, 2010 has been disclaimed.

[21] Appl. No.: 215,628

[22] Filed: Mar. 22, 1994

[30] Foreign Application Priority Data

Apr. 1, 1993 [GB] United Kingdom ............... 9306886

[51] Int. Cl.$^6$ .................. A61K 31/165; C07C 233/04
[52] U.S. Cl. .................. 514/620; 514/618; 514/617; 514/619; 564/162; 564/163; 564/164; 564/165; 564/167; 564/168; 564/171
[58] Field of Search ............ 564/171, 163, 161; 514/620, 619, 617

[56] References Cited

U.S. PATENT DOCUMENTS

| | | |
|---|---|---|
| 4,049,663 | 9/1977 | Harper et al. |
| 4,513,009 | 4/1985 | Roques et al. |
| 4,631,287 | 12/1986 | Chakraborty et al. |
| 4,639,468 | 1/1987 | Roncucci et al. |
| 4,725,619 | 2/1988 | Chakraborty et al. |
| 4,728,668 | 3/1988 | Chakraborty et al. |
| 4,839,369 | 6/1989 | Youssefyeh et al. |
| 5,236,957 | 8/1993 | Dostert et al. |

FOREIGN PATENT DOCUMENTS 0400495 12/1990 European Pat. Off.
1140748 1/1969 United Kingdom.
WO90/14334 11/1990 WIPO.

OTHER PUBLICATIONS

Eur. Neuropsychopharmacol. 1/ 317-319, 1991, P. Dostert, et al., "New Anticonvulsants With Selective MAO-B Inhibitory Activity".

*Primary Examiner*—Shailendra Kumar
*Attorney, Agent, or Firm*—Oblon, Spivak, McClelland, Maier & Neustadt

[57] ABSTRACT

The invention provides new compounds of formula (I)

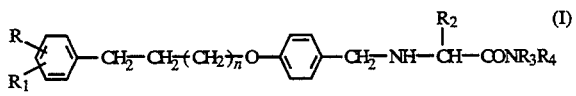

wherein, subject to a proviso, n is zero or an integer of 1 to 3; each of R and $R_1$, which may be the same or different, is hydrogen, halogen, trifluoromethyl or $C_1$-$C_4$ alkoxy; $R_2$ is hydrogen or $C_1$-$C_4$ alkyl optionally substituted by hydroxy; each of $R_3$ and $R_4$ independently is hydrogen or $C_1$-$C_4$ alkyl; or a pharmaceutically acceptable salt thereof; and of formula (IA)

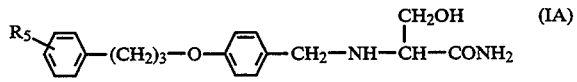

wherein $R_5$ is hydrogen, halogen, trifluoromethyl or $C_1$-$C_4$ alkoxy, or a pharmaceutically acceptable salt thereof, which are active on the central nervous system (CNS) and can be used in therapy as anti-epileptics, anti-Parkinson, neuroprotective, antidepressant, antispastic and hypnotic agents.

8 Claims, No Drawings

SUBSTITUTED (ARYLALKOXYBENZYL)AMINOPROPANAMIDE DERIVATIVES AND PROCESS FOR THEIR PREPARATION

The present invention relates to substituted (phenylalkoxybenzyl)aminopropanamide derivatives, to their use as therapeutic agents, to a process for their preparation and to pharmaceutical compositions containing them.

Other N-substituted α-amino carboxamide derivatives are known as having pharmacological properties, for instance those described by British patent No. 1140748. The compounds according to this prior art document are useful in the treatment and prophylaxis of such diseases as coronary artery disease and atherosclerosis; moreover they are useful in the treatment of inflammatory conditions such as rheumatoid arthritis.

Further substituted amino acid derivatives are known as enkephalinase inhibitors, analgesics and hypotensives from EP-A-0038758.

Still other substituted glycine and alanine derivatives are disclosed by US-A-4049663. The compounds according to this document have utility as oral analgesics.

WO-90/14334 discloses N-phenylalkyl substituted α-aminocarboxamide derivatives active on the central nervous system.

It has now been found that novel substituted (arylalkoxybenzyl)aminopropanamide derivatives as herein defined have valuable biological properties, in particular as anti-epileptic, anti-Parkinson, neuroprotective, antidepressant, antispastic, and/or hypnotic agents. Accordingly, the present invention provides a new compound of formula (I)

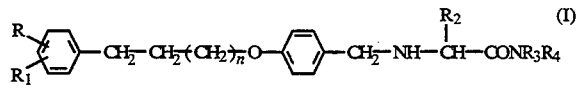

wherein
n is zero or an integer of 1 to 3;
each of R and $R_1$, which may be the same or different, is hydrogen, halogen, trifluoromethyl or $C_1$–$C_4$ alkoxy;
$R_2$ is hydrogen or $C_1$–$C_4$ alkyl optionally substituted by hydroxy;
each of $R_3$ and $R_4$ independently is hydrogen or $C_1$–$C_4$ alkyl; or a pharmaceutically acceptable salt thereof; and
wherein when, at the same time, n is zero, 1 or 2, $R_2$ is hydrogen or unsubstituted $C_1$–$C_4$ alkyl and R and $R_1$ are as defined above, then $R_3$ and $R_4$ are both hydrogen; and
wherein when, at the same time, R and $R_1$ are hydrogen, n is zero or 1 and $R_2$ is methyl, then at least one of $R_3$ and $R_4$ is other than hydrogen.

A—$(CH_2)_n$— group may be a branched or straight alkylene chain.

A halogen atom is preferably fluorine, chlorine or bromine, in particular fluorine or chlorine.

A $C_1$–$C_4$ alkoxy group may be a branched or straight group, typically methoxy, ethoxy, propoxy, isopropoxy, butoxy or tert-butoxy, preferably methoxy or ethoxy.

A $C_1$–$C_4$ alkyl group may be a branched or straight group, typically methyl, ethyl, propyl, isopropyl, butyl or tert-butyl, preferably methyl or ethyl.

A $C_1$–$C_4$ alkyl group substituted by hydroxy is typically hydroxymethyl.

Preferred compounds of the invention are the compounds of formula (I) wherein, subject to the above proviso, n is as defined above;
R is hydrogen and $R_1$ is hydrogen, halogen or $C_1$–$C_4$ alkoxy;
$R_2$ is $C_1$–$C_4$ alkyl;
$R_3$ and $R_4$ are hydrogen; and the pharmaceutically acceptable salts thereof.

Specific examples of preferred compounds of the invention are:
2-[4-(5-phenylpentyl)oxybenzyl]aminopropanamide;
2-{4-[2-(2-fluorophenyl)ethyl]oxybenzyl}aminopropanamide;
2-{4-[2-(3-fluorophenyl)ethyl]oxybenzyl}aminopropanamide;
2-[4-(4-phenylbutyl)oxybenzyl]aminopropanamide;
2-{4-[3-(2-fluorophenyl)propyl]oxybenzyl}aminopropanamide;
2-{4-[3-(3-fluorophenyl)propyl]oxybenzyl}aminopropanamide;
2-{4-[3-(4-fluorophenyl)propyl]oxybenzyl}aminopropanamide;
2-{4-[3-(2-chlorophenyl)propyl]oxybenzyl}aminopropanamide;
2-{4-[3-(3-chlorophenyl)propyl]oxybenzyl}aminopropanamide;
2-{4-[3-(4-chlorophenyl)propyl]oxybenzyl}aminopropanamide;
2-{4-[3-(2-bromophenyl)propyl]oxybenzyl}aminopropanamide;
2-{4-[3-(3-bromophenyl)propyl]oxybenzyl}aminopropanamide;
2-{4-[3-(2,6-dichlorophenyl)propyl]oxybenzyl}aminopropanamide;
2-{4-[3-(3-methoxyphenyl)propyl]oxybenzyl}aminopropanamide;
2-{4-[3-(2-methoxyphenyl)propyl]oxybenzyl}aminopropanamide;
2-[4-(3-phenylpropyl)oxybenzyl]amino-3-hydroxy-N-methylpropanamide;
if the case, either as single (S) or (R) isomer or as a mixture thereof; and the pharmaceutically acceptable salts thereof, The present invention also provides a compound of the following formula (IA)

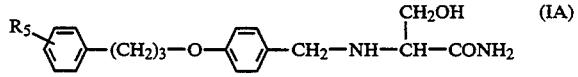

wherein $R_5$ is hydrogen, halogen, trifluoromethyl or $C_1$–$C_4$ alkoxy; or a pharmaceutically acceptable salt thereof. Compounds of formula (IA) are a selected class of compounds according to WO-90/14334.

Preferred compounds of formula (IA) are those wherein $R_5$ is hydrogen or halogen; and the pharmaceutically acceptable salts thereof.

Specific examples of preferred compounds of formula (IA) are the following:
2-[4-(3-Phenylpropyl)oxybenzyl]amino-3-hydroxypropanamide;

2-{4-[3-(2-fluorophenyl)propyl]oxybenzyl}amino-3-hydroxypropanamide;

2-[4-[3-(3-fluorophenyl)propyl]oxybenzyl}amino-3hydroxypropanamide;

if the case, either as single (R) or (S) isomer or as a mixture thereof; and the pharmaceutically acceptable salts thereof.

The compounds of formulae (I) and (IA) and their salts are hereafter referred to as the "active compounds" and as the "compounds of the invention".

The present invention includes all the possible optical isomers of the compounds of formulae (I) and (IA) and their mixtures, as well as the metabolites thereof. The present invention also includes within its scope pharmaceutically acceptable bioprecursors and prodrugs of the compounds of formulae (I) and (IA), i.e. compounds, which have a formula different to formulae (I) and (IA), respectively, but which nevertheless are directly or indirectly converted in vivo into a compound of formulae (I) or (IA), respectively, upon administration to a human being.

Pharmaceutically acceptable salts of the compounds of formulae (I) and (IA) include acid addition salts with inorganic acids, e.g. nitric, hydrochloric, hydrobromic, sulphuric, perchloric, and phosphoric acid, or organic acids, e.g. acetic, propionic, glycolic, lactic, oxalic, malonic, malic, tartaric, citric, benzoic, cinnamic, mandelic, methanesulfonic and salicylic acids.

The compounds of formula (I) and the pharmaceutically acceptable salts thereof can be obtained by a process comprising a) reacting a compound of formula (II)

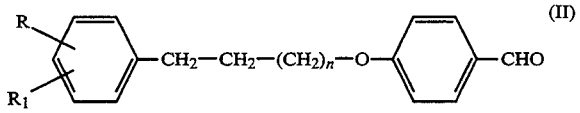

wherein R, R$_1$ and n are as defined above with a compound of formula (III)

wherein R$_2$, R$_3$ and R$_4$ are as defined above; or b) reacting a compound of formula (IV) or a reactive derivative thereof

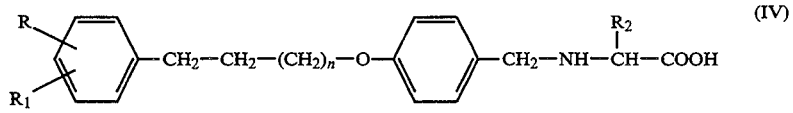

wherein R, R$_1$, n and R$_2$ are as defined above, with an amine of formula (V)

HNR$_3$R$_4$      (V)

wherein R$_3$ and R$_4$ are as defined above; or c) reacting a compound of formula (VI)

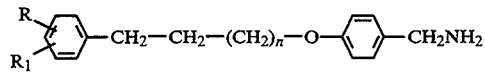

wherein R, R$_1$ and n are as defined above, with a compound of formula (VII)

wherein R$_2$, R$_3$, and R$_4$ are as defined above and W is a halogen atom; and, if desired, converting a compound of formula (I) into another compound of formula (I), and/or, if desired, converting a compound of the invention into a pharmaceutically acceptable salt and/or, if desired, converting a salt into a free compound and/or, if desired, separating a mixture of isomers of compounds of the invention into the single isomers.

All the processes described hereabove are analogy processes and can be carried out according to well known methods in organic chemistry.

The reaction of a compound of formula (II) with a compound of formula (III) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride. Occasionally, molecular sieves can be added to the reaction mixture for facilitating the reaction.

A reactive derivative of a compound of formula (IV) may be for instance an alkyl ester thereof, e.g. a C$_1$–C$_6$ alkyl ester such as a C$_1$–C$_4$ alkyl ester and, in particular a methyl, ethyl or propyl ester, which may be unsubstituted or substituted by a phenyl ring optionally substituted by a nitro group.

Preferably an alkyl ester of a compound of formula (IV) is used.

The reaction of a compound of general formula (IV) or a reactive derivative thereof and an amine of formula (V) can be performed using an excess of the amine, optionally in the presence of water or of an organic solvent, such as dimethylformamide. The temperature of the reaction may range from about 20° C. to about 100° C.

In a compound of formula (VII) W is preferably bromine or chlorine. The reaction of a compound of general formula (VI) with a compound of general formula (VII) can be carried out in a suitable organic solvent, such as an alcohol, e.g. ethanol, or in dimethylformamide, at a temperature ranging from about 40° C. to about 140° C. in the presence of a suitable acid acceptor, e.g. anhydrous potassium carbonate, or triethylamine.

A compound of the invention can be converted, as stated above, into another compound of the invention by known methods.

Also the optional salification of a compound of the invention as well as the conversion of a salt into the free compound and the separation of a mixture of isomers into the single isomers may be carried out by conventional methods.

The compounds of formulae (II) to (VII) are either known compounds or may be obtained according to known methods, e.g. as described in WO-90/14334, or in the Examples which follow.

The compounds of formula (IA) and the pharmaceutically acceptable salts thereof can be obtained by any one of process variants a) to c) described above for the preparation of compounds of formula (I).

The compounds of formula (IA) and the pharmaceutically acceptable salts thereof are preferably obtained by a process comprising reacting a compound of formula (VIII).

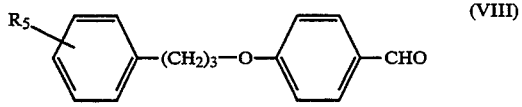

wherein $R_5$ is as defined above; with a compound of formula (IX)

and if desired converting a compound of formula (IA) into a pharmaceutically acceptable salt, and/or, if desired, converting a salt into a free compound, and/or, if desired, separating a mixture of isomers of a compound of formula (IA) into the single isomers.

The reaction of a compound of formula (VIII) with a compound of formula (IX) can be carried out by following the same reaction conditions described above in connection with the reaction of a compound of formula (II) with a compound of formula (III).

Also the additional optional process steps described above as well as the salification of a compound of formula (IA) can be performed according to known methods. When in the compounds of the present invention and in the intermediate products thereof groups are present, which need to be protected before submitting them to the hereabove illustrated reactions, they may be protected before being reacted and then deprotected, according to methods well known in organic chemistry.

The intermediate compounds, according to the processes herein described for the preparation of the compounds of the invention, may be either in the form of a single isomer or as a mixture thereof. Preferably they are in the form of a single isomer.

PHARMACOLOGY

The compounds of the invention are active on the central nervous system (CNS) and can be used in therapy, for example as antiepileptics, in the treatment of Parkinson's disease and as neuroprotective agents, e.g. in degenerative processes associated with normal ageing or pathological situations, such as brain ischemia; they can also be used as antidepressants, hypnotics and antispastic agents. The activity on the CNS of the compounds of the invention was evaluated on the basis of pharmacological methods, such as, for example, the antagonism of convulsions and lethality induced by intravenous injection of bicuculline in mice (Antiepileptic Drugs, D. M. Woodbury et al. eds., 2nd edition, Raven Press, New York, 1982), or the antagonism of maximal electroshock seizures (MES) (Woodbury, L. A. and Davenport V. D., Arch. Int. Pharmacodyn. Ther. 92; 97–104, 1952).

The neurotoxicity of the compound and of the reference anticonvulsants was assessed with the rotorod test (Dunan and Miye., J. Am. Pharm. Ass. Sci. Ed., 1957, 46, 208; Kinnard et al., J. Pharmacol. Exp. Ther. 1957, 121, 354; Horowitz. Nature, 1963, 200, 369).

For instance, the following Table 1 summarizes the activity and neurotoxicity data obtained in the MES test and in the rotorod test, respectively, for a representative group of compounds according to the present invention, in comparison with the prior art compound 2-[4-(3-phenylpropyl)oxybenzyl]aminopropanamide methanesulfonate (internal code FCE 27023) which is known from WO-90/14334

| Internal Code FCE | MES-ED$_{50}$ (mg/kg) | ROTOROD-TD$_{50}$ (mg/kg) | TI |
|---|---|---|---|
| 28243 | 12.4 | 1005 | 82 |
| 28244 | 12.5 | 1011 | 81 |
| 28238 | 10.6 | 1581 | 149 |
| 28115 | 15.9 | >2000 | >125 |
| 28239 | 14.8 | 1166 | 79 |
| 28245 | 8.6 | 863 | 100 |
| 27023 | 8.8 | 584 | 66 | wherein:
ED$_{50}$ means effective dose in 50% of treated animals
TD$_{50}$ means toxic dose in 50% of treated animals
TI means therapeutic index (TD$_{50}$/ED$_{50}$)
FCE 28243 means 2-{4-[4-phenylbutyl]oxybenzyl}aminopropanamide, methanesulfonate
FCE 28244 means 2-{4-[5-phenylpentyl]oxybenzyl}aminopropanamide, methanesulfonate
FCE 28238 means 2-(4-[3-chlorophenyl)propyl]oxybenzyl}aminopropanamide, methanesulfonate
FCE 28115 means 2-{4-[3-fluorophenyl)propyl]oxybenzyl}aminopropanamide, methanesulfonate
FCE 28239 means 2-{4-[3-chlorophenyl)propyl]oxybenzyl}aminopropanamide, methanesulfonate
FCE 28245 means 2-{4-[3-phenylpropyl)oxybenzyl]amino-3-hydroxy-propanamide, methanesulfonate.

From the above comparative test data it is evident that the compounds of the present invention are endowed with a better therapeutic index than the prior art compounds. A patient is treated according to the present invention by a method comprising administering to the patient an effective amount of one of the compounds of the invention. In this way the present compounds can be used to treat disorders of the central nervous system, for example epilepsy or Parkinson's disease; or as neuroprotective agents, anti-depressants, hypnotics or antispastic agents. The condition of a patient may thus be improved.

The compounds of the invention can be administered in a variety of dosage forms, e.g. orally, in the form of tablets, capsules, sugar- or film-coated tablets, liquid solutions; rectally, in the form of suppositories; parenterally, e.g. intramuscularly or by intravenous injection or infusion. The therapeutic regimen for the different clinical syndromes must be adapted to the type of pathology taking into account, as usual, also the route of administration, the form in which the compound is administered and the age, weight and conditions of the subject involved.

The oral route is employed, in general, for all conditions requiring such compounds. In emergency situations preference is given to intravenous injection. For these purposes the compounds of the invention can be administered orally at doses ranging e.g. from about 20 to about 1500 mg/day. Of course, these dosage regimens may be adjusted to provide the optimal therapeutic response.

The nature of the pharmaceutical composition containing the compounds of this invention in association with pharmaceutically acceptable carriers or diluents will, of course, depend upon the desired route of administration. The composition may be formulated in the conventional manner with the usual ingredients. For example, the compounds of the invention may be administered in the form of aqueous or oily solutions or suspensions, tablets, pills, gelatine capsules, syrups, drops or suppositories.

Thus, for oral administration, the pharmaceutical compositions containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example by means of mixing, granulating, tabletting, sugar-coating or film-coating processes.

The liquid dispersions for oral administration may be, e.g., syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and, if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

Diethyl 2-(2-fluorobenzyl)malonate 5.6 g (0.243 g.a.) of metal sodium were carefully dissolved in abs. EtOH (145 ml) under a nitrogen atmosphere. At the end of the dissolution, 62 ml (0.408 mol) of diethylmalonate and 26.9 ml (0.205 mol) of 2-fluorobenzylchloride were added. The mixture was kept at 50° C. for 5 hours, then cooled to room temperature and allowed to stand overnight. After evaporation, the crude residue was taken up with water and extracted with ethyl acetate. The extracts were washed with brine and dried over an. sodium sulfate. The crude oil obtained after evaporation was distilled at 132° C./0.8 mm/Hg to provide 49 g (73%) of diethyl 2-(2-fluorobenzyl)malonate.

EXAMPLE 2

3- (2-fluorophenyl) propionic acid 49 g (0.183 mol) of diethyl 2-(2-fluorobenzyl)malonate were mixed with 183 ml of 37% HCl and 9.4 ml of glacial acetic acid. The mixture was heated at reflux for 27 hours, then cooled; the solid precipitated was filtered, taken up with water, basified with sat. NaHCO$_3$, washed with diethyl ether, then reacidified with 20% HCl, extracted with diethyl ether and washed with brine. After drying and evaporation, the oily residue was taken up with petroleum ether: upon freezing a white solid precipitated (21.5 g; 70%).

EXAMPLE 3

3-(2-fluorophenyl))propan-1-ol 21 g (0.125 mol) of 3-(2-fluorophenyl)propionic acid were dissolved in THF. While stirring and cooling at 0° C., under a nitrogen atmosphere, 11.8 g (0.311 mol) of sodium borohydride were added, and 78 ml (0.636 mol) of BF$_3$.Et$_2$O dropped. Stirring at 0° C. was continued for 1 h, then, 200 ml of (1:1) water:methanol were carefully added. The mixture was evaporated, taken up with water, extracted with ethyl acetate; the organic phase was washed with brine, dried and evaporated. The crude oil obtained was flash-chromatographed on silica gel (eluant: chloroform 190-methanol 10) to furnish a colorless fluid (12.8 g; 67%).

EXAMPLE 4

3-(2-fluorophenyl) propyl methanesulfonate 12.7 g of 3-(2-fluorophenyl)propan-1-ol (0.0824 mol) were dissolved in CH$_2$Cl$_2$ (250 ml) and the mixture was kept to 5° C., under nitrogen. 11.5 ml of triethylamine were added, followed by 6.35 ml of methanesulfonyl chloride in CH$_2$Cl$_2$ (20 ml) while maintaining the temperature at 5° C. The mixture was kept to room temperature, washed with brine; the organic phase was dried and evaporated to give an oil (18.5 g; 97%).

EXAMPLE 5

4-(3 -(2-fluorophenyl)propyl)oxybenzaldehyde

To a suspension of 55% sodium hydride (3.34 g; 0.08 mol) in DMF (180 ml), at room temperature under nitrogen, 9.7 g (0.08 mol) of 4-hydroxybenzaldehyde were added; the mixture was heated to 50° C., then 18.5 g (0.08 mol) of 3-(2-fluorophenyl)propyl) methanesulfonate in 20 ml of DMF were dropped. The temperature was kept to 70° C. and maintained for 1 hour. The solvent was removed, the residue taken up with water, extracted with ethyl acetate, washed with brine, dried over an. Na$_2$SO$_4$, evaporated to provide an oil which was further purified by flash-chromatography on silica gel (eluant: cyclohexane 8 : ethyl acetate 2). A colourless oily residue was obtained (15 g; 73%).

EXAMPLE 6

(S)-2-[4-(3-(2-fluorophenyl)propyl)oxybenzyl]aminopropionamide

To a solution of (S)-(+)-2-aminopropanamide (1.93 g; 0170 mol) in anhydrous methanol (60 ml), under stirring and nitrogen, 2.0 g of 4 Å molecular sieves were added and then, in a single portion, NaBH$_3$CN (0.78 g; 0.0124 mol); after 10 minutes, 4 g (0.0155 mol) of 4-(3-(2-fluorophenyl)propyl) oxybenzaldehyde were added, in 20 ml of anhydrous methanol. After 3 hours, the reaction was completed, the mixture was filtered, the filtrates washed with methanol, the residue was directly flash-chromatographed on silica gel (eluant: CH$_2$Cl$_2$ 195: CH$_3$OH 5: 30% NH$_4$OH 0.5) to give a white solid (2.7 g; 53%). The free base thus obtained was treated with a stoichiometric amount of methanesulfonic acid to yield (S)-(+) 2-{4-[3-(2-fluorophenyl)propyl)oxybenzyl}aminopropanamide, methanesulfonate; m.p. 172°–177° C.; $[\alpha]^{25}$+10.4 (C=1.06, AcOH).

Analogously, starting from the same aldehyde and (R)-(+) -2-aminopropanamide, the R-enantiomer of the title compound can be obtained; m.p. 177°–180° C.; $[\alpha]^{22}$ −11.5 (C=1.09, AcOH ).

Analogously, the following compounds can be obtained starting from the appropriate aldehyde and (R) or (S) -α-aminoamide either in the (S)- or (R)- enantiomeric form.

2-{4-[3-(3-fluorophenyl)propyl]oxybenzyl}aminopropanamide methanesulfonate; m.p. 150°–152° C.

2-{4-[2-(2-fluorophenyl)ethyl]oxybenzyl}aminopropanamide methanesulfonate; m.p. 176°–180° C.

2-{4-[2-(3-fluorophenyl)ethyl]oxybenzyl}aminopropanamide methanesulfonate; m.p. 165°–168° C.

2-{4-[5-phenylpentyl]oxybenzyl}aminopropanamidemethanesulfonate; m.p. 162°–165.5° C.

2-{4-[4-phenylbutyl]oxybenzyl}aminopropanamide methanesulfonate; m.p. 165°–168° C.

2-{4-[3-(4-fluorophenyl)propyl]oxybenzyl}aminopropanamide methanesulfonate; m.p. 173°–176° C.

2-{4-[3-(2-chlorophenyl)propyl]oxybenzyl}aminopropanamide methanesulfonate; m.p. 170° C. (dec.)

2-{4-[3-(3-chlorophenyl)propyl]oxybenzyl}aminopropanamide methanesulfonate; m.p. 152.5°–155° C.

2-{4-[3-(4-chlorophenyl)propyl]oxybenzyl}aminopropanamide methanesulfonate;

2-{4-[3-(2-bromophenyl)propyl]oxybenzyl}aminopropanamide methanesulfonate; m.p. 171°–173° C. (dec.)

2-{4-[3-(3-bromophenyl)propyl]oxybenzyl}aminopropanamide methanesulfonate; m.p. 140° C. (dec.)

2-{4-[3-(2,6-dichlorophenyl)propyl]oxybenzyl}aminopropanamide methanesulfonate;

2-{4-[3-(3-methoxyphenyl)propyl]oxybenzyl}aminopropanamide methanesulfonate; m.p. 154°–156.5° C.

2-{4-[3-(2-methoxyphenyl)propyl]oxybenzyl}aminopropanamide methanesulfonate; m.p. 127.5°–129.5° C.

2-[4-(3-phenylpropyl)oxybenzyl]amino-3-hydroxypropanamide methanesulfonate; m.p. 115° C. (dec.)

2-{4-[3-(2-fluorophenyl)propyl]oxybenzyl}amino-3-hydroxypropanamide methanesulfonate;

2-{4-[3-(3-fluorophenyl)propyl]oxybenzyl}amino-3-hydroxypropanamide methanesulfonate; and 2-[4-(3-phenylpropyl)oxybenzyl]amino-3-hydroxy-N-methylpropanamide methanesulfonate; m.p. 95°–101° C.

EXAMPLE 7

Tablets, each weighing 300 mg and containing 100 mg of active substance can be manufactured as follows:
Composition (for 5000 tablets)
2-{4-[3-(3-fluorophenyl)propyl]oxybenzyl}

| | |
|---|---|
| aminopropanamide methanesulfonate | 500 g |
| Lactose | 710 g |
| Corn starch | 237.5 g |
| Talc powder | 37.5 g |
| Magnesium stearate | 15 g |

2-{4-[3-(3-fluorophenyl)propyl]oxybenzyl}aminopropanamide methanesulfonate hydrochloride, lactose and half of the corn starch are mixed; the mixture is then forced through a sieve of 0.5 mm openings. Corn starch (18 g) is suspended in warm water (180 ml).

The resulting paste is used to granulate the powder. The granules are dried, comminuted on a sieve of sieve size 1.4 mm, then the remaining quantity of starch, talc and magnesium is added, carefully mixed, and processed into tablets.

We claim:

1. A compound of formula (I)

$$R\text{-}\underset{R_1}{\underset{|}{\bigcirc}}\text{-}CH_2\text{-}CH_2(CH_2)_n\text{-}O\text{-}\bigcirc\text{-}CH_2\text{-}NH\text{-}\underset{R_2}{\underset{|}{CH}}\text{-}CONR_3R_4 \quad (I)$$

wherein n is zero or an integer of 1 to 3;

each of R and R$_1$, which may be the same or different, is hydrogen, halogen, trifluoromethyl or C$_1$–C$_4$ alkoxy;

R$_2$ is hydrogen or C$_1$–C$_4$ alkyl optionally substituted by hydroxy;

each of R$_3$ and R$_4$ independently is hydrogen or C$_1$–C$_4$ alkyl; or a pharmaceutically acceptable salt thereof; and wherein when, at the same time, n is zero, 1 or 2, R$_2$ is hydrogen or unsubstituted C$_1$–C$_4$ alkyl and R and R$_1$ are as defined above, then R$_3$ and R$_4$ are both hydrogen; and wherein when, at the same time, R and R$_1$ are hydrogen, n is zero or 1 and R$_2$ is methyl, then at least one of R$_3$ and R$_4$ is other than hydrogen.

2. A compound of formula (I), according to claim 1, wherein n is as defined in claim 1;

R is hydrogen and R$_1$ is hydrogen, halogen or C$_1$–C$_4$ alkoxy;

R$_2$ is C$_1$–C$_4$ alkyl; and

R$_3$ and R$_4$ are hydrogen; or a pharmaceutically acceptable salt thereof.

3. A compound which is

2-{4-[2-(2-fluorophenyl)ethyl]oxybenzyl}aminopropanamide;

2-{4-[2-(3-fluorophenyl)ethyl]oxybenzyl}aminopropanamide;

2-[4-(4-phenylbutyl)oxybenzyl]aminopropanamide;

2-{4-[3-(2-fluorophenyl)propyl]oxybenzyl}aminopropanamide;

2-{4-[3-(3-fluorophenyl)propyl]oxybenzyl}aminopropanamide;

2-{4-[3-(4-fluorophenyl)propyl]oxybenzyl}aminopropanamide;

2-{4-[3-(2-chlorophenyl)propyl]oxybenzyl}amino-
propanamide;

2-{4-[3-(3-chlorophenyl)propyl]oxybenzyl}amino-
propanamide;

2-{4-[3-(4-chlorophenyl)propyl]oxybenzyl}amino-
propanamide;

2-{4-[3-(2-bromophenyl)propyl]oxybenzyl}amino-
propanamide

2-[4-(5-phenylpentyl)oxybenzyl]aminopropanamide;

2-{4-[3-(3-bromophenyl)propyl]oxybenzyl}amino-
propanamide;

2-{4-[3-(2,6-dichlorophenyl)propyl]oxybenzyl-
}aminopropanamide;

2-{4-[3-(3-methoxyphenyl)propyl]oxybenzyl}amino-
propanamide;

2-{4-[3-(2-methoxyphenyl)propyl]oxybenzyl}amino-
propanamide;

2-[4-(3-phenylpropyl)oxybenzyl]amino-3-hydroxy-
N-methylpropanamide;

if the case, either as single (S) or (R) isomer or as a mixture thereof; or a pharmaceutically acceptable salt thereof.

4. A compound of formula (IA)

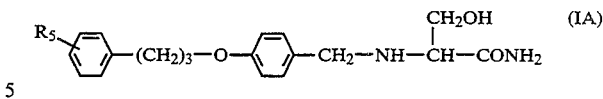

wherein $R_5$ is hydrogen, halogen, trifluoromethyl or $C_1$-$C_4$ alkoxy; or a pharmaceutically acceptable salt thereof.

5. A compound of formula (IA) according to claim 4 wherein $R_5$ is hydrogen or halogen; or a pharmaceutically acceptable salt thereof.

6. A compound which is
2-[4-(3-phenylpropyl)oxybenzyl]amino-3-hydroxy-
propanamide;
2-{4-[3-(2-fluorophenyl)propyl]oxybenzyl}amino-3-
hydroxy-propanamide;
2-{4-[3-(3-fluorophenyl)propyl]oxybenzyl}amino-3-
hydroxy-propanamide;

if the case, either as single (R) or (S) isomer or as a mixture thereof; or a pharmaceutically acceptable salt thereof.

7. A pharmaceutical composition comprising a pharmaceutically acceptable carrier and/or diluent and, as an active principle, a compound of formula (I) or (IA) as defined in any one of claims 1 to 6 or a pharmaceutically acceptable salt thereof.

8. A method of treating a patient suffering from epilepsy, comprising:
administering to the patient a therapeutically effective amount of the compound of formula (I) or (IA), as defined in claim 1 or 4, or a pharmaceutically acceptable salt thereof.

* * * * *